United States Patent [19]
Steer et al.

[11] Patent Number: 5,647,861
[45] Date of Patent: Jul. 15, 1997

[54] OSTOMY COUPLING

[75] Inventors: Peter L. Steer, Sussex; Keith G. M. Hollands, Sompting; Graham Emery Steer, London; Ronald A. Plass, West Sussex; Howard Barratt, Surrey, all of England

[73] Assignee: E. R. Squibb & Sons, Inc., Princeton, N.J.

[21] Appl. No.: 634,158

[22] Filed: Apr. 12, 1996

[30] Foreign Application Priority Data

Apr. 13, 1995 [GB] United Kingdom ............... 9507666

[51] Int. Cl.$^6$ ........................................ A61F 5/44
[52] U.S. Cl. ............... 604/342; 604/338; 215/279; 215/280
[58] Field of Search ................... 604/332, 338, 604/339, 342–344; 215/274, 275, 279, 280, 286

[56] References Cited

U.S. PATENT DOCUMENTS 5,026,360  6/1991  Johnson et al. .................. 604/339

FOREIGN PATENT DOCUMENTS

572378B1  12/1993  European Pat. Off. ............ 604/338

*Primary Examiner*—Robert A. Clarke
*Attorney, Agent, or Firm*—Stuart E. Krieger

[57] ABSTRACT

It would be desirable to have improved designs of ostomy couplings which embody a springy or resilient split ring as a locking ring.

In an ostomy coupling, first and second coupling members 80, 90 are held together by a springy flexible split locking ring 100. A plurality of tabs 101 symmetrically arranged on each limb of the locking ring 100, can be withdrawn generally radially outwardly by movement of the locking ring to permit separation of the two coupling members. The split ring 100 is for the most part circular in its unstressed condition.

4 Claims, 1 Drawing Sheet

OSTOMY COUPLING

BACKGROUND OF THE INVENTION

This invention relates to an ostomy coupling.

Ostomy couplings are used to connect and disconnect a bag for receiving a stomal discharge to and from a medical grade adhesive pad which is applied to the peristomal area of the skin of the wearer. Many designs of ostomy coupling are known. One which has enjoyed considerable commercial success is described and claimed in U.K. Patent No. 1,571,657.

An ostomy coupling in which unlocking of two coupling parts is achieved by deforming a ring is disclosed in our U.K. Patent Application No. 9409037.0, which was filed 6 May 1994 but was published after the filing of this application.

In PCT Application W091/01119, published 1991 and corresponding to European Patent 482 104B, there is disclosed a locking ring for an ostomy coupling. An ostomy coupling which embodies such a ring is shown in European Patent 572 378B. Features of this design are that inwardly sprung tongues on the ring peripherally surround the joined coupling parts and that a press-button engagement device as well as a hook and detent engagement device are included, apparently in a quest for secure retention of the locking ring on the coupling parts. It appears inevitable that quite intricate manipulation of this design of coupling is needed when applying or removing the bag.

It has been proposed by Kubo, in Japanese Utility Model No. 62-11610, published February 1985, that an ostomy device should have a double female ring structure which can interengage with a male ring. The male ring may be on the bag and the female ring on a skin-attachable adhesive pad, or vice-versa. The outer ring on the female ring is circular and flexible and has a pair of inwardly-extending catches at opposite ends of a diameter. By pressing on two diametrically extending lugs, whose diameter is substantially at right angles to the diameter joining the catches, the outer female ring is deformed so that the catches are caused to move radially outwardly, so permitting separation of the two coupling parts.

This arrangement, though perhaps operable in theory, has serious disadvantages in practice, for example (i) to connect or disconnect it is necessary to hold the coupling at four places, approximately spaced at 90° intervals around the periphery, (ii) pressing on two diametrically opposed regions will tend to bend the coupling out of its normal plane and the forces applied may easily cause the body side pad to be partially (or wholly) detached from the skin of the wearer, also the need to press in both ends of the diameter fully, and simultaneously, means that releasing the bag-side coupling is subject to uncertainty, (iii) the repeated attachment and withdrawal of the bag-side coupling part will cause the o-ring (provided to prevent escape of excreted matter between the male and female rings) to become worn, so compromising its sealing qualities with potentially highly embarrassing and undesirable results, (iv) the wearer may find it difficult to determine whether or not the two coupling pans are properly engaged, (v) the accuracy and forces needed for manipulation to connect or disconnect will be well beyond the capability of an infirm, confused, elderly or impatient wearer; (vi) it is hard to be sure that the appliance is properly locked; and (vii) in the case of large sizes, the old and infirm will find it physically difficult to span with their hand and push in diametrally opposed regions of the ring.

SUMMARY OF THE INVENTION

It is an aim of this invention to provide an improved design of ostomy couplings which embodies a springy or resilient split ring as a locking ring.

According to one aspect of the present invention, there is provided an ostomy coupling in which first and second coupling members are held together by a springy flexible split locking ring and in which a plurality of tabs, arranged on the limbs of the locking ring, can be withdrawn generally radially outwardly by movement of the locking ring to permit separation of the two coupling members; the locking ring being arranged so that its limbs can be deformed in substantially opposed horizontal directions.

According to another aspect of the invention, there is provided an ostomy copuling in which first and second coupling members are held together by a springy flexible split locking ring comprising two limbs, and in which a plurality of tabs, symmetrically arranged on each limb of the locking ring, can be withdrawn generally radially outwardly by substantially horizontal forces on the limbs of the locking ring to permit separation of the two coupling members in a direction substantially axially of the coupling.

It will be understood that the movement of the locking ring which causes withdrawal of the tabs is a deformation of the ring in opposed approximately horizontal directions.

The invention will be better understood from the following non-limiting description of an example thereof given with reference to the accompanying drawings in which:

DETAILED DESCRIPTION OF THE INVENTION

The illustrated and preferred ostomy coupling comprises first and second coupling members 80 and 90 and a split locking ring 100. The first coupling member may be a plastics moulding and may be made of low density polyethylene. The second coupling member may also be a plastics moulding, e.g. of EVA.

For the material of the locking ring, good results have been achieved with an acetal copolymer known as 'KEMATAL' (Registered Trade Mark) which is also referred to as polyoxymethylene (POM) and is available from Hoechst. This is crystalline thermoplastic with an exceptionally stable polymer structure; a suitable grade is 'HOSTAFORM' (Registered Trade Mark) C. 27021.

Figure 3:
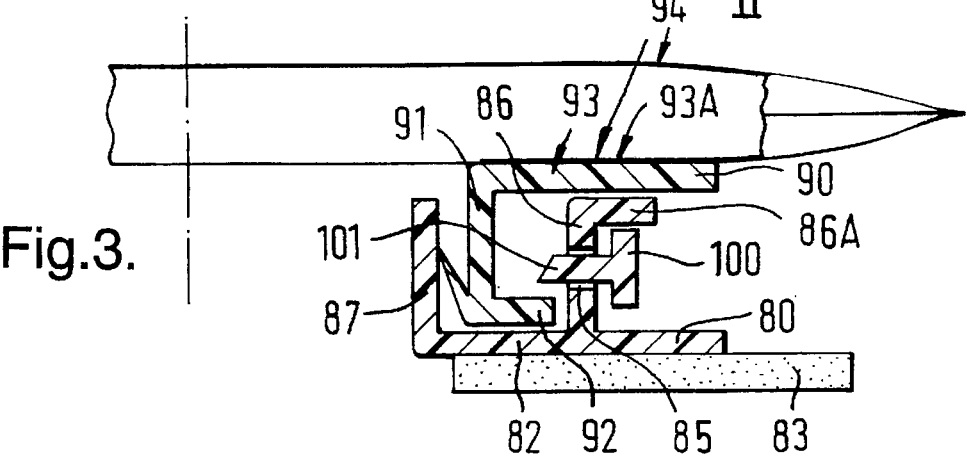
FIG. 3 is a cross-sectional view on the plane II—II in FIG. 2 showing the way in which the locking ring can lock together the fast and second coupling members.

The first coupling member 80 has a cylindrical wall 87 which surrounds the stomal orifice. A flange 82 forms part Of the member 80 and is attached to a medical grade adhesive pad 83. The coupling member 80 also has a wall 86 which together with a wall 87 defines a channel within which can be received part of the coupling member 90, as seen in FIG. 3. The wall 86 has a radially outwardly extending flange 86A which serves to define an annular channel within which the locking ring 100 is received. The wall 86 has apertures (one shown at 85) through which the tabs 101 project radially inwards in the locked condition of the coupling.

The medical grade adhesive pad may comprise a base which is preferably a thin film of polymeric material such as polyethylene and an adhesive layer situated on the rear surface of a base. Such an adhesive layer is preferably formed as a homogeneous blend of one or more pressure-sensitive viscous or elastomeric materials having intermittently dispersed therein one or more water-soluble or swellable hydrocolloid gums and may also include one or more thermoplastic elastomers and/or one or more swellable cohesive strengthening agents. Such an adhesive pad is shown at 83, FIG. 3.

The second coupling member 90 comprises a wall 91, a flange 93, and a lesser diameter flange 92. To the surface 93A of the flange 93, an ostomy pouch 94 can be attached in any suitable manner, e.g. by adhesive. A resilient seal strip 96 is integral with the coupling member 90 and extends radially inwardly into contact with the external surface of the wall 87, which bounds the stomal orifice. The function of the seal strip is to prevent leakage and to take up any minor tolerance variations which may have arisen in the moulding operation by which the member 90 is manufactured.

Figure 1:
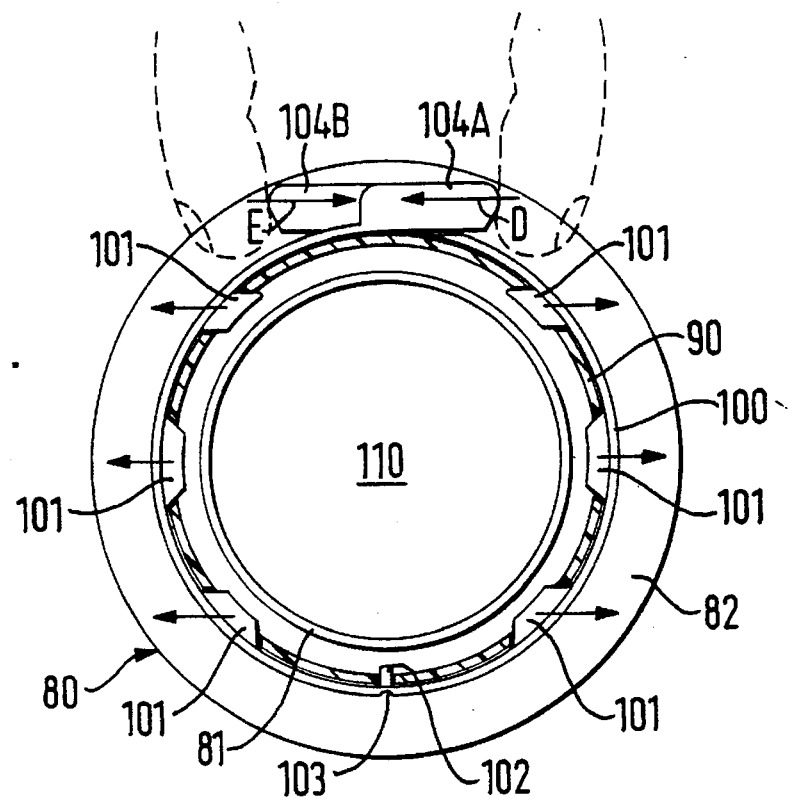
FIG. 1 is a plan view of an example of the invention, showing a first coupling member and a locking ring, the second coupling member having been temporarily removed to expose the construction.
Figure 2:
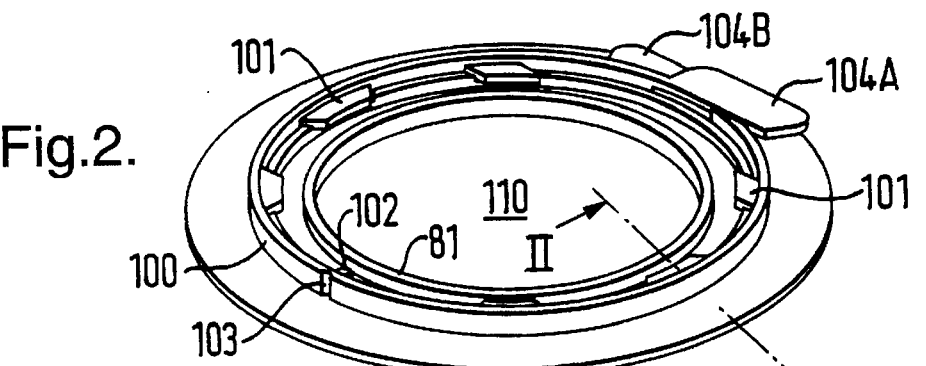
FIG. 2 is a perspective view of the pans shown in FIG. 1.

The locking ring 100 is generally circular in shape but is split at its "top dead centre" (or 12 o-clock) region. The ring at that region has end portions 104A and 104B one of which is in front of the other. As seen in FIG. 1, by placing a thumb on one end of portion 104A and a finger on the opposite end of portion 104B, and squeezing, the ring, which is springy and resilient and may be made of acetal resin, is caused to "open", that is, deform outwardly. This outward deformation, caused by opposed forces applied in the direction of the arrows D and E, results in the tabs 101 moving outwardly through the apertures 85. This causes the tabs 101 to clear the apertures 85. A lug 102 is radially-inwardly directed and is provided on the split locking ring 100. This extends into a suitable recess (not referenced) in the second coupling member 90. In the same region, there is a cut out 103 in the outside of the split locking ring 100. This weakens the ring 100 at its mid-point so as to enable the ring to be opened more easily, when pressure is applied as indicated by arrows D and E. Once the tabs 101 have cleared the apertures 85, the first and second coupling members can be readily separated. It will be understood that modifications, alterations, and improvements could be made to the invention. For example, instead of having coupling members which are circular, it would be possible for them to be oval or of other closed loop shape. While the preferred material for the locking ring in each embodiment is an acetal resin, other plastics materials having the appropriate flexible and springy characteristics could be employed. Other specific mechanisms could be employed to actuate the tabs of the split locking ring. The resilient or deflectible sealing strip may be provided on either the coupling member 80 or 90 to reduce the possibility of leakage and to take up any tolerances between the coupling members which may arise in manufacture.

What is claimed is:

1. An ostomy coupling comprising:

first and second coupling members capable of being coupled together, each of said members having a central stomal opening, said first coupling member having a flange with a projection-receiving channel, said channel being defined at least in part by a concentric inner wall and outer wall, said inner wall being positioned closer to said stomal opening, said outer wall having a plurality of tab-receiving slots extending therethrough, said second coupling member having a projection receivable in said channel when said first and second members are properly pushed together, said projection being lockable in said channel, and a resilient, circular, releasably lockable locking ring positionable circumferentially about said outer wall, said locking ring including a plurality of tabs projecting radially inwardly, said tabs being extendable through said slots so as to restrain said projection in said channel when said locking ting is in a latched condition, said tabs being withdrawable from said slots when said locking ring is released into an open condition, said locking ring having two ends that are latched to form said locked condition, and unlatched to form said open condition.

2. The ostomy coupling of claim 1 wherein said projection includes an offset portion that extends substantially perpendicular to said channel walls, said rim portion being restrained from being removable from said channel by said tabs when said locking ring is in said locked condition.

3. The ostomy coupling of claim 1 wherein said locking ring includes an area of weakening to facilitate opening of said locking ring.

4. The ostomy coupling of claim 1 wherein said projection includes a deflectable seal to help eliminate any leakage when said first and second coupling members are coupled together.

* * * * *